United States Patent [19]

Carlson

[11] 4,187,376
[45] Feb. 5, 1980

[54] REMOVAL OF CONTAMINANTS FROM CYANURIC ACID REACTION PRODUCT

[75] Inventor: Ronald H. Carlson, Willingboro, N.J.

[73] Assignee: FMC Corporation, Philadelphia, Pa.

[21] Appl. No.: 835,653

[22] Filed: Sep. 22, 1977

[51] Int. Cl.$^2$ .......................................... C07D 251/32
[52] U.S. Cl. ..................... 544/192; 203/28; 203/58
[58] Field of Search ........................................ 544/192

[56] References Cited

U.S. PATENT DOCUMENTS

| | | | |
|---|---|---|---|
| 2,357,028 | 8/1944 | Shiras et al. | 203/58 |
| 2,368,597 | 1/1945 | Morris et al. | 203/58 |
| 3,065,233 | 11/1962 | Hopkins et al. | 544/192 |
| 3,117,963 | 1/1964 | Merkel et al. | 544/192 |
| 3,164,591 | 1/1965 | Walles et al. | 544/192 |
| 3,563,987 | 2/1971 | Berkowitz | 544/192 |
| 3,635,968 | 1/1972 | Goelz et al. | 544/192 |
| 3,994,892 | 11/1976 | Den Otter et al. | 544/192 |

FOREIGN PATENT DOCUMENTS

| | | | |
|---|---|---|---|
| 146806 | 11/1972 | Czechoslovakia | 544/192 |
| 2300037 | 7/1974 | Fed. Rep. of Germany | 544/192 |
| 950826 | 2/1964 | United Kingdom | 260/248 A |

*Primary Examiner*—John M. Ford
*Attorney, Agent, or Firm*—Frishauf, Holtz, Goodman & Woodward

[57] ABSTRACT

Unreacted urea and/or biuret contaminants in a cyanuric acid-inert solvent reaction product are removed by distilling the solvent therefrom at a temperature of from about 150° C. to about 250° C. and at a pressure of from about 70 to about 170 mm. of Hg. A distillate of said solvent containing the urea, biuret and a cyanuric acid reaction product is collected.

11 Claims, 1 Drawing Figure

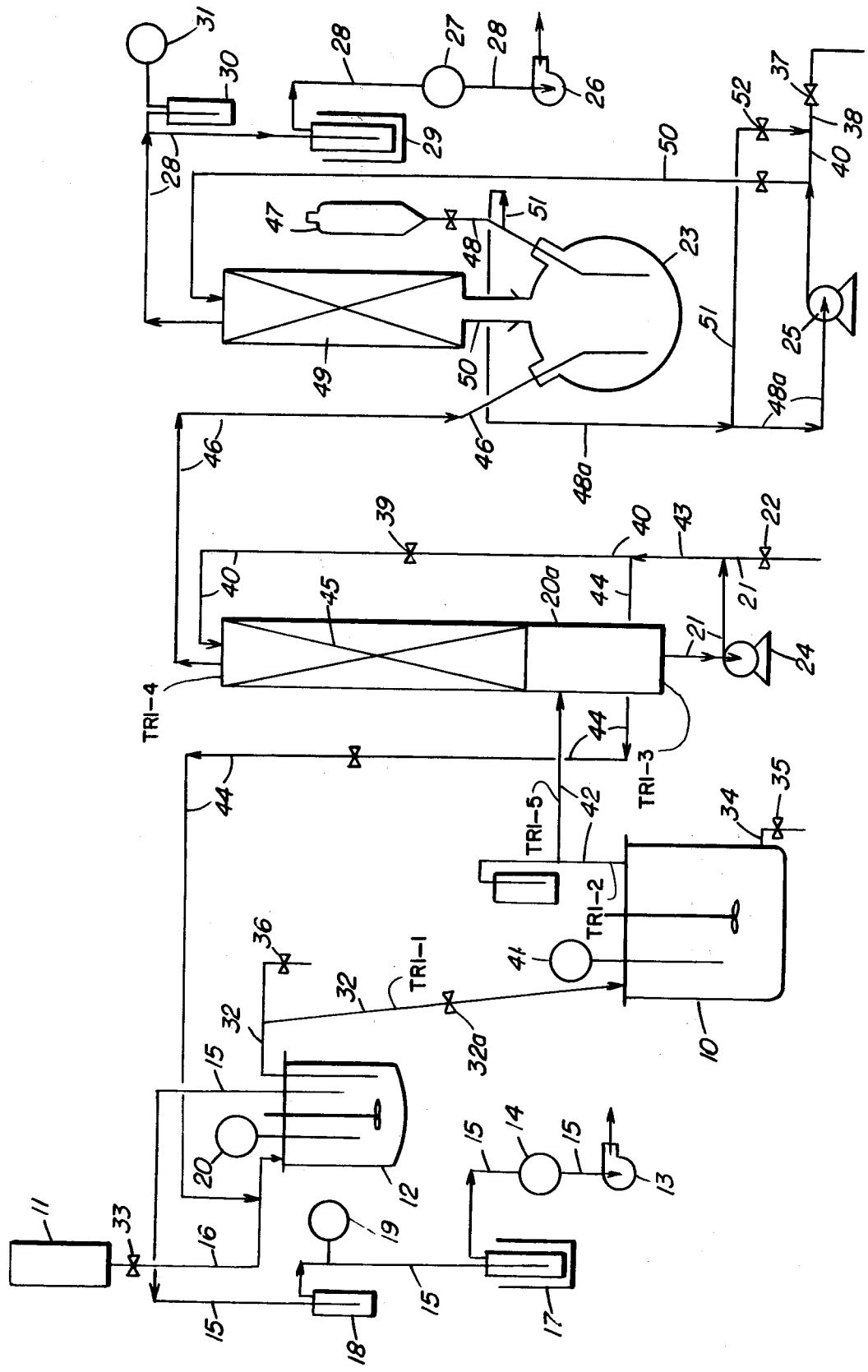

REMOVAL OF CONTAMINANTS FROM CYANURIC ACID REACTION PRODUCT

BACKGROUND OF THE INVENTION

1. Field of the Invention

This invention has to do with removal of urea and/or biuret from a cyanuric acid - inert solvent reaction product, and more particularly from such a reaction product obtained by pyrolytic conversion of urea or biuret in the presence of the inert solvent.

2. Description of the Prior Art

As described in U.S. Pat. No. 3,563,987 and in the art identified therein, it is known that cyanuric acid can be produced by the pyrolysis of urea in an inert solvent, as shown by the equation:

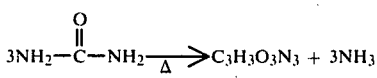

wherein $C_3H_3O_3N_3$, cyanuric acid (CA, hereinafter), is represented as

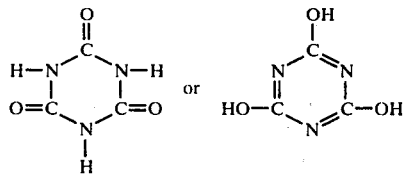

Inert solvents which are advantageous for the pyrolysis have a boiling point of at least about 180° C. at pressures up to about 250 mm. of Hg., readily dissolve urea and biuret, have limited solubility for CA, and are not chemically reactive with urea, biuret and CA. Such solvents include alkyl sulfones and cyclic sulfones, such as sulfolane (tetramethylene sulfone).

Residual unpyrolyzed urea/biuret co-precipitates with CA on cooling a sulfolane reaction slurry and contaminates the resulting filter cake, which is subsequently purified. The presence of urea/biuret in a CA cake is undesirable from both a process efficiency and operability standpoint. For maximum sulfolane process efficiency, operability and final CA purity, the levels of urea and biuret in a reactor product cake should be as low as possible (e.g., >1% each). Higher levels than this require greater energy and water consumption in achieving satisfactory CA purification.

It is an object of this invention, therefore, to provide a process to meet the desired urea/biuret impurity levels in a CA reactor cake which is subsequently purified. Such purification is necessary in order to meet accepted product quality specifications and standards.

SUMMARY OF THE INVENTION

In accordance with the present invention, there is provided a process for removing urea, biuret or a mixture thereof contained in a mixture of CA and an inert solvent. The process comprises distilling the CA-inert solvent mixture at a temperature of from about 150° C. to about 250° C. and at a pressure of from about 70 to about 170 mm. of Hg., and removing a distillate therefrom comprising the inert solvent and substantially all of the urea, biuret or mixture of urea and biuret. Thus, the urea, biuret or mixture thereof is co-distilled with the solvent.

DESCRIPTION OF THE INVENTION AND PREFERRED EMBODIMENTS

The invention is not limited to any particular reaction mechanism; however, a likely mechanism for removing urea values (urea, biuret or mixtures thereof) from a CA-inert solvent mixture containing such values involves pyrolytic dissociation of urea and biuret to isocyanic acid and ammonia, with subsequent recombination of isocyanic acid with ammonia, urea or itself to form urea (or ammonium cyanate), biuret or CA, respectively, on relatively colder condenser surfaces of the distillation equipment employed. These relationships are shown by equations (1) through (3):

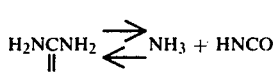

(urea)

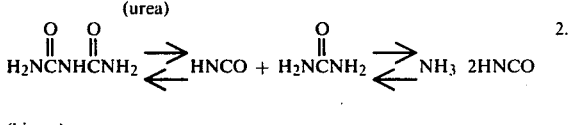

(biuret)

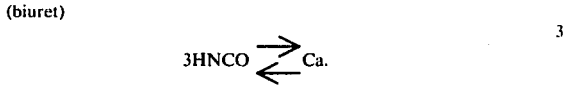

In the distillation, co-volatilized inert solvent serves as a sweep gas to increase the rate of $NH_3$ and HNCO removal from the mixture being distilled. In addition, solvent vapor removal from the distillation vessel employed into another vessel (i.e., distillation as opposed to reflux) acts to prevent mechanical wash back of condensed urea value vapors into the distillation vessel. Thus, a distinguishing feature of the process of this invention is that the inert solvent is allowed to distill from the mixture being distilled or from a CA reaction product, so as to sweep residual unreacted urea values therefrom. Solvent distillation as opposed to previously taught solvent reflux is a prerequisite for effective removal of residual unreacted urea values.

Inert solvents such as described in the process of U.S. Pat. No. 3,563,987 are preferred herein, with sulfolane (tetramethylene sulfone) being particularly preferred. For convenience, the contents of U.S. Pat. No. 3,563,987 are incorporated herein by reference, and the invention is illustrated with sulfolane as the solvent.

Pyrolytic conversion of urea or biuret to CA is carried out in a reactor at a temperature of from about 150° C. to about 250° C., at a pressure of from about 70 to about 170 mm. of Hg. and a residence time of from about 2 to about 120 minutes. Preferred conditions are 180°–220° C., 80–120 mm. of Hg., and 5–60 minutes.

A condenser connected to the reactor for condensing a distillate of sulfolane and urea values is operated at a temperature of from about 25° to about 75° C., preferably 30°–55° C. The distillation rate is from about 1 to about 25, preferably 2–15, grams per minute. The amount of sulfolane distilled can be up to about 60 percent by volume of the sulfolane present, and is preferably from 10 to 35 percent.

In the pyrolytic conversion of urea or biuret to CA, the amount of unreacted urea and/or biuret is generally from 0.01 to about 5 percent by weight. Preferably, in the process of this invention, the amount of each is from about 0.05 to about 3 percent of each of these compounds, with a combined total of about 5 percent.

The process can be carried out either in a batch or continuous operating mode.

The following examples are given to illustrate the invention and are not deemed to be limiting thereof. Examples 1 to 9 illustrate batch operation, and Examples 10 through 17 illustrate continuous operation.

Examples 1–3 show the effect of pressure and temperature at substantially constant hold (residence) time. Examples 4–6 show the effect of hold time at substantially constant pressure and temperature. Examples 7–9 show the effect of heat input and reflux to distillate ratio (R/D) at substantially constant hold time, temperature and pressure.

EXAMPLES 1–3

In a first series of runs, three experiments were conducted covering maximum temperature and pressure ranges of 195° C. (~80 mm.Hg.) to 220° C. (~160 mm.Hg.). A typical experiment was run as follows: A total of 250 g. of sulfolane "W" was placed into a 500 ml. 3-neck flask, equipped with a Claisen head and a water cooled condenser, and heated under vacuum to drive off water. The flask can be considered to simulate a reactor/stripper. At the onset of sulfonane distillation, the unit was pressurized back to one atmosphere and 25 g. CA and 5 g. each of urea and biuret were added to the sulfolane, sufficient to give a slurry composition of ~9% CA and 2% of each of urea and biuret. The slurry was then heated for 45 minutes at the desired temperature/pressure range with magnetic stirring to effect sulfolane distillation. A phosphoric acid trap (150 g. of 20% $H_3PO_4$) was incorporated down-stream of the sulfolane condenser to collect evolved $NH_3$. At the end of the reaction period, the pot slurry was cooled and weighed, along with the distillate and $H_3PO_4$ trap liquor. Accumulated solids in the water-cooled condenser were washed out with acetone. Samples were analyzed for CA, urea, biuret, $NH_3$ and $NH_4OCN$. Data are presented in Tables I and II and show that virtually complete (98%) removal of urea and biuret from the simulated reaction slurries was achieved under all process operating conditions, where 33–45% of the initial solfolane charge was distilled. The simulated slurry represents a composition corresponding to approximately 90% conversion of a 16.6% solution of urea to CA and biuret.

In each of the three experiments, $NH_3$ balance was 100 ±10%. HNCO balance generally ran high due to apparent analytical sampling difficulties with pot slurries. Data in Table I were further analyzed to show the amount of urea and biuret removed from the simulated reaction slurry by distillation (and subsequent condensation to urea, biuret and CA) vs. in-situ conversion (to CA). The data are presented in Table III and show that increased in-situ conversion to CA is favored by high temperature-high pressure conditions. A greater "stripping action" is achieved under lower temperature-higher vacuum conditions.

All distillates were collected at ~20°–25° C. and contained suspended solids. Material seemed to precipitate from the distillate as it cooled in travelling the length of the condenser barrel. The bulk of the precipitated solids washed along with the condensed sulfolane; that remaining adhered to the condenser surfaces appeared to be high in $NH_4OCN$ content.

EXAMPLES 4–6

A second series of three batch experiments was performed as described in Examples 1–3, except that previously distilled anhydrous sulfolane rather than sulfolane "W" was used. Again, the initial slurry weighed 275 g. and contained 25 g. CA and 5 g. each of urea and biuret. Data are presented in Tables IV and V and show, as expected a steady decrease in removal efficiency with decrease in residence time. Again, no significant difference between rates of urea and biuret removal (i.e., conversion) was noted.

EXAMPLES 7–9

Another series of three batch experiments was conducted in the same manner as in Examples 1–3 to investigate the effects of heat input and total sulfolane reflux on urea and biuret removal efficiency. Data are presented in Tables VI and VII and show in general that stripping efficiency increases with an increase in the amount of sulfolane distilled from a slurry. The effect is most pronounced in going from a total reflux to a partial (4% of input sulfolane) distillation condition. At least partial sulfolane distillation is required to prevent vaporized and recondensed urea values from washing back into the reaction slurry. In this series of experiments, the sulfolane condenser was air-cooled rather than $H_2O$-cooled, as was the case in Examples 1–6. Due to the resulting higher distillate temperature, a marked reduction in ammonium cyanate ($NH_4OCN$) content in the distillate was noted.

The data from all batch stripping experiments are tabulated in Table VIII and show that stripping efficiency is a function of both residence time in the reactor/stripper and relative amount of sulfolane distilled (heat input). As can be seen from the data, the profiles for urea and biuret removal are essentially the same. The influence of residence time is simply a kinetic effect, allowing urea and biuret sufficient time to dissociate (ultimately) into HNCO and $NH_3$, with subsequent vaporization or in-situ polymerization to CA. The influence of sulfolane distillation is felt in two ways: first, as a kinetic strip gas effect, and second, as a mechanical action preventing wash back of vaporized/recondensed urea values.

The batch stripping data further show in Table IX a general increase in in-situ conversion of stripped urea and biuret to CA with decrease in level of sulfolane distillation. Relative (to $NH_3$) volatility of HNCO therefore appears to increase with increased sulfolane take-off, due probably to entrainment and sweep gas effects.

TABLE I

UREA/BIURET STRIPPING FROM SIMULATED REACTOR SLURRY[3]
Effect of Pressure/Temperature Variation

| Operating Conditions | | | | Stream Analysis | | | | | |
|---|---|---|---|---|---|---|---|---|---|
| T°C. | Press. (mm.Hg.) | Time (min.) | Stream | Wt.(g.) | % CA | % Urea | % Biuret | % $NH_3$ | % $NH_4OCN$ |
| 180–195 | 85 | 45 | pot | 168.0 | 18.0 | 0.014 | N.D. | 0.04 | — |
| | | | distillate | 142.6[1] | 2.49 | 1.03 | 0.92 | 0.51 | — |

TABLE I-continued
UREA/BIURET STRIPPING FROM SIMULATED REACTOR SLURRY[3]
Effect of Pressure/Temperature Variation

| Operating Conditions | | | Stream Analysis | | | | | | |
|---|---|---|---|---|---|---|---|---|---|
| T°C. | Press. (mm.Hg.) | Time (min.) | Stream | Wt.(g.) | % CA | % Urea | % Biuret | % NH$_3$ | % NH$_4$OCN |
| | | | trap | 124.4[1] | — | — | — | 0.75 | — |
| 180–205 | 105–115 | 45 | pot | 177.5 | 16.1 | N.D. | 0.026 | 0.002 | — |
| | | | distillate | 90.6 | 2.14 | 1.83 | 1.46 | 0.036 | N.D.[4] |
| | | | trap | 146.7 | — | — | — | 1.03 | — |
| 180–219 | 154–162 | 55 | pot | 190.8 | 18.2 | 0.038 | N.D. | 0.018 | — |
| | | | distillate[2] | 85.0 | 2.58 | 1.03 | 0.53 | 0.235 | — |
| | | | trap | 139.2 | — | — | — | 1.14 | N.D.[4] |

[1]H$_3$PO$_4$ trap liquor backed up into distillate receiver.
[2]I.R. and elemental analysis of condenser solids showed the presence of high concentrations of NH$_4$OCN.
[3]Composition: 240 g. Sulfolane W, 25 g. CA, 5 g. urea, 5 g. biuret Sulfolane W - 97% (weight) sulfolane, 3% (weight) water.
[4]Non-Detectable.

TABLE II
UREA/BIURET STRIPPING FROM SIMULATED REACTOR SLURRY[1]
Effect of Pressure/ Temperature Variation

| Operating Conditions | | | % Removal from Reactor Slurry | |
|---|---|---|---|---|
| Time (min.) | Temp. (°C.) | Press. (mmHg) | % Sulfolane Distilled | Urea | Biuret |
| 45 | 180–195 | 85 | 45.4 | 99.5 | 100 |
| 45 | 180–205 | 105–115 | 35.0 | 100 | 99.1 |
| 55 | 180–219 | 154–162 | 33.0 | 98.6 | 100 |

[1]Composition: 9.1% CA, 1.8% Urea, 1.8% Biuret

TABLE V
UREA/BIURET STRIPPING FROM SIMULATED REACTOR SLURRY[1]
Effect of Hold Time

| Operating Conditions | | | % Sulfolane Distilled | % Removal From Reactor Slurry | |
|---|---|---|---|---|---|
| Time (min.) | Temp. (°C.) | Press. (mmHg) | | Urea | Biuret |
| 15 | 196–198 | 78 | 10.5 | 85.3 | 91.7 |
| 10 | 196–200 | 82–84 | 15.3 | 80.6 | 78.8 |
| 5 | 196–199 | 82 | 3.0 | 59.8 | 54.4 |

[1]Composition: 9.1% CA, 1.8% Urea, 1.8% Biuret

TABLE III
IN-SITU CONVERSION OF STRIPPED UREA/BIURET IN SIMULATED REACTOR SLURRY

| Operating Conditions | | | Total HNCO[1] Released in Reactor Slurry (g.) | Total HNCO[2] Recovered in Distillate (g.) | Total HNCO[3] Converted in Reactor Slurry (g.) | % Conversion in Reactor Slurry |
|---|---|---|---|---|---|---|
| T°C. | Press. (mm.Hg.) | Time (min.) | | | | |
| 180–195 | 85 | 45 | 7.74 | 5.70 | 2.04 | 26.4 |
| 180–205 | Ψ–115 | 45 | 7.72 | 4.23 | 3.49 | 45.2 |
| 180–219 | 154–162 | 55 | 7.71 | 3.19 | 4.51 | 58.6 |

[1]from net urea/biuret removal
[2]recovered as urea, biuret and CA; NH$_4$OCN contribution considered negligible.
[3]calculated by difference.

TABLE IV
UREA/BIURET STRIPPING FROM SIMULATED REACTOR SLURRY[1]
Effect of Hold Time

| Operating Conditions | | | Stream Analysis | | | | | | |
|---|---|---|---|---|---|---|---|---|---|
| T°C. | Press. (mm.Hg.) | Time (min.) | Stream | Wt. (g.) | % CA | % Urea | % Biuret | % NH$_3$ | % NH$_4$OCN |
| 196–198 | 78 | 15 | pot | 244.6 | 11.79 | 0.30 | 0.17 | 0.0073 | — |
| | | | distillate | 28.0 | 0.56 | 4.07 | 3.19 | ~0 | ~2.2 |
| | | | trap | 141.6 | — | — | — | 0.61 | — |
| 196–200 | 82–84 | 10 | pot | 236.0 | 12.63 | 0.41 | 0.45 | 0.0153 | — |
| | | | distillate | 39.0 | 0.35 | 1.97 | 1.59 | 0.13 | 2.03 |
| | | | trap | 149.9 | — | — | — | 0.73 | — |
| 196–199 | 82 | 5 | pot | 264.8 | 11.33 | 0.76 | 0.86 | 0.0192 | — |
| | | | distillate | 7.8 | — | 3.39 | 2.15 | ~0 | ~2.5 |
| | | | trap | 147.6 | — | — | — | 0.51 | — |

[1]Composition: 240 g. Sulfolane, 25 g. CA, 5 g. Urea, 5 g. Biuret

TABLE VI
UREA/BIURET STRIPPING FROM SIMULATED REACTOR SLURRY[1]
Effect of Heat Input and Total Reflux

| Operating Conditions | | | | Stream Analysis | | | | | | |
|---|---|---|---|---|---|---|---|---|---|---|
| T°C. | Press. (mmHg) | Time (min) | Heat (Watts) | Stream | Wt(g) | % CA | % Urea | % Biuret | % NH$_3$ | % NH$_4$OCN |
| 180–196 | 84 | 32 | 130 | pot | 252.2 | 11.41 | 0.21 | 0.076 | 0.0117 | N.D.[2] |
| | | | | distillate | 19.47 | 0.56 | 5.58 | 3.70 | 0.22 | N.D.[2] |
| | | | | trap | 150.6 | — | — | — | 0.81 | — |
| 180–197 | 84 | 40 | 106 | pot | 246.3 | 11.87 | 0.16 | 0.16 | 0.0095 | N.D.[2] |
| | | | | distillate | 10.32 | 0.78 | 7.65 | 4.49 | 0.11 | N.D.[2] |
| | | | | trap | 148.5 | — | — | — | 0.90 | — |
| 180–195 | 84 | 16 | 107 | pot | 274.8 | 11.44 | 0.53 | 0.49 | 0.12 | N.D.[2] |

TABLE VI-continued
UREA/BIURET STRIPPING FROM SIMULATED REACTOR SLURRY[1]
Effect of Heat Input and Total Reflux

| Operating Conditions | | | | Stream Analysis | | | | | | |
|---|---|---|---|---|---|---|---|---|---|---|
| T°C. | Press. (mmHg) | Time (min) | Heat (Watts) | Stream | Wt(g) | % CA | % Urea | % Biuret | % NH$_3$ | % NH$_4$OCN |
| | | | | distillate | 0.0 | — | — | — | — | — |
| | | | | trap | 148.3 | N.D.[2] | — | — | 0.95 | — |

[1]Composition: 240 g. sulfolane, 25 g. CA, 5 g. urea, 5 g. biuret.
[2]Non-Detectable.

TABLE VII
UREA/BIURET STRIPPING FROM SIMULATED REACTOR SLURRY[1]
Effect of Heat Input and Total Reflux

| Operating Conditions | | | % Sulfolane Distilled | Heat Input (Watts) | % Removal From Reactor Slurry | |
|---|---|---|---|---|---|---|
| Time (min) | Temp (°C.) | Press. (mmHg) | | | Urea | Biuret |
| 32 | 180–196 | 84 | 7.3 | 130 | 89.4 | 96.2 |
| 40 | 180–197 | 84 | 3.7 | 106 | 92.1 | 92.1 |
| 16 | 180–195 | 84 | 0 | 107 | 70.8 | 73.0 |

[1]Composition: 9.1% CA, 1.8% Urea, 1.8% Biuret

TABLE VIII
EFFECT OF RESIDENCE TIME AND SULFOLANE DISTILLATION ON UREA/BIURET STRIPPING EFFICIENCY[2]

| Residence Time[1] (min.) | % Sulfolane Distilled | % Removal from Slurry | |
|---|---|---|---|
| | | Urea | Biuret |
| 45 | 45.4 | 99.5 | 100 |
| 45 | 35.0 | 100 | 99.1 |
| 55 | 33.0 | 98.6 | 100 |
| 40 | 3.7 | 92.1 | 92.1 |
| 32 | 7.3 | 89.4 | 96.2 |
| 15 | 10.5 | 85.3 | 91.7 |
| 10 | 15.3 | 80.6 | 78.8 |
| 16 | 0 | 70.8 | 73.0 |
| 5 | 3.0 | 59.8 | 54.4 |

[1]at reactor temperature > 180° C.
[2]initial slurry (275 g.) composition: 9.09% CA   1.82% Urea   1.82 Biuret

TABLE IX
EFFECT OF SULFOLANE DISTILLATING ON IN-SITU CONVERSION OF STRIPPED UREA/BIURET TO CA

| % Sulfolane Distilled | % In-Situ Conversion in Reaction Slurry[1] |
|---|---|
| 45.4 | 26.4 |
| 35 | 45.2 |
| 33 | 58.6 |
| 15.3 | 65.2 |
| 10.5 | 59.4 |
| 7.3 | 79.2 |
| 3.7 | 85.5 |
| 3.0 | 88.5 |
| 0 | 100 |

[1]Calculated by difference between amount converted in reactor slurry and amount collected in distillate.

EXAMPLES 10–17

These continuous examples are described in conjunction with the illustrative flow diagram shown in the drawing.

Continuous stripper/reactor 10 was started up according to the following procedure. Reservoir 11 was filled with a feed solution comprising 1000 ml. of ~3% urea in sulfolane. The contents of feed tank 12, comprising ~1300 ml. heel (undistilled reaction product) from a previous run, were heated to 120° C., and the pressure in 12 was reduced to 200 mmHg. via pump 13, control valve 14 and line 15. Reservoir 11 and feed tank 12 are joined by line 16. Liquid traps 17 and 18, and pressure indicator 19 are included in line 15. The temperature in feed tank 12 was monitored at 120°±5° C. by thermocouple control 20 appropriately positioned therein. All heaters (not shown) were turned on and the contents of reactor/stripper 10, comprising ~500 ml. heel from a previous run, were heated to 200° C. Solution level in sulfolane condenser/scrubber 20a was adjusted to ~50 ml. by draw-off through line 21 and sampling valve 22. H$_3$PO$_4$ reservoir 23 was filled with 4 liters of 25% H$_3$PO$_4$ and pumps 24 and 25 were turned on. Pressure of the system was reduced to ~95 mmHg. via pump 26, control valve 27 and line 28. Liquid traps 29 and 30, and pressure indicator 31 are included in line 28.

Once temperature/pressure equilibrium in the system had been achieved, flows to feed tank 12 from 11 through line 16 and from 12 to reactor/stripper 10 through line 32, and heat input to reactor/stripper 10 were set to achieve the desired residence time/sulfolane distillation condition. For each experimental condition, the system was operated for a period of two residence times to reach steady state. The liquid level in feed tank 12 was maintained constant (at ~1300 ml.) by balancing the flow out of 12 through line 32 and valve 32a against pre-set flow into 12 through valve 33 required to achieve the desired residence time. Liquid level in reactor/stripper 10 was maintained constant at 500 ml. by frequent sample withdrawal through line 34 and valve 35. At the end of the two-residence-time stabilization period, reservoir 11 was refilled and samples (~50 ml.) were withdrawn from vessels 12, 10, 20a and 23 through valves 36 (line 32), 35 (line 34), 22 (line 21) and 37 (line 38), respectively. The liquid level in condenser/scrubber 20a was also adjusted to ~175 ml.

The system was then run as previously described for a period of two residence times at steady state. During steady state operation, the sulfolane re-circulation rate in condenser/scrubber 20a was maintained at ~175 ml./min. by adjustment of control valve 39 in line 40. If necessary to prevent overflow, sulfolane level in condenser/scrubber 20a was reduced by solution withdrawal through valve 22. At the end of the steady state period, the volume of feed added to feed tank 12 was recorded and sulfolane level in 20a was reduced via valve 22 to the original pre-set value (~175 ml.). All solution collected from reactor/stripper 10 and condenser/scrubber 20a during steady state operation was composited and weighed. Samples were withdrawn from feed tank 12 and reservoir 23 and analyzed along with the vessel 10 and 20a composites and the previous set of four samples taken at the beginning of steady state operation. Samples were analyzed for urea, biuret, CA, NH3 and cyanate content.

As shown, the temperature of reactor/stripper 10 can be monitored by thermometer 41 therein.

Distillate from reactor/stripper 10 is removed through line 42 to a lower section of condenser/scrubber 20a. Sulfolane condensed in 20a can be recycled through lines 21 (including pump 24) and 43 and valved line 44 to line 16 and/or via valved line 40 to an upper (scrubbing) section 45 of 20a.

Gaseous materials from scrubbing section 45 are removed overhead from 20a through line 46 to H3PO4 reservoir 23.

H3PO4 can be added to reservoir 23 from storage 47 via valved line 48. NH3 scrubber 49 is connected to reservoir 23 through line 50.

H3PO4 can also be passed from line 48 to line 48a containing pump 25 to valved line 50 for use in NH3 scrubber 49 or removal through lines 48a and 51, valve 52 and line 38 containing valve 37.

Temperatures are recorded at stations identified by TR1-1 through TR1-5.

CONTINUOUS OPERATION

An initial block of six runs shows the effect of heat input and residence time on the efficiency of urea and biuret removal from a simulated sulfolane reaction product. Due to the low solubility of biuret in sulfolane leading to pluggage and feed measurement problems, a feed consisting of about 3% urea in sulfolane was chosen for this block of runs. In two preliminary runs, a feed consisting of ~1% urea and 0.3-0.7% biuret was used. In the block of six runs, flow rate was controlled to maintain a residence time in reactor/stripper 10 having a 500 ml. operating volume of either 15 or 30 minutes. Heat input was controlled to achieve three levels of sulfolane distillation at each residence time: 10-15, 20-25 and 35-45%. Heat was supplied to feed and reaction vessels, as well as to solution transfer lines. Vessel temperature/pressure profiles and temperature recording point profiles for each of the total of eight runs (2 shake down plus 6 block runs) conducted are presented in Table X. Analytical and urea/biuret conversion data (over two residence times) are presented in Tables XI and XII, respectively, and show:

1. As found with the batch studies, efficiency of urea/biuret removal increased with increased heat input (sulfolane distillation) and residence time.

2. Greater than 90% removal of urea/biuret was obtained (from a feed containing ~1% urea, ~0.5% biuret) at ~200° C./100 mmHg. over a 30 minute residence time, with a sulfolane distillation level of 50%.

3. At comparable residence time/sulfolane distillation levels, urea removal in the continuous runs was 15-20% lower (in absolute terms) than observed in the batch experiments; total HNCO value (as urea+biuret) removal was 25-40% lower.

4. Efficiency of biuret removal by reaction/stripping decreased with increase in urea/biuret ratio in feed. At feed ratios greater than about 10/1, a net biuret removal would no longer occur.

5. At a 30 minute residence time, 80% removal of urea+biuret values (expressed as HNCO) was achieved at ~200° C./100 mmHg. at a level of 20-30% sulfolane distillation.

6. Decreasing residence time to 15 minutes decreased total urea/biuret removal from 80% to 60-70% at the same distillation level (20-30%).

7. At a 30 minute residence time, about 30% of the urea+biuret values removed in reactor/stripper 10 were reacted in-situ to CA; the balance were distilled from reactor/stripper 10 and condensed in condenser/scrubber 20a (and to a very small extent in ammonia scrubber 49) in the form of urea, biuret, CA and to a very limited extent, ammonium cyanate.

8. At a 15 minute residence time, in-situ conversion to CA increased to 40-60%.

9. NH3 solubility in sulfolane was relatively independent of system pressure, composition and temperature and ranged from 50-200 ppm in all streams.

10. Sulfolane mass balance around the system was essentially quantitative.

A material balance for total urea+biuret recovery (as HNCO) is presented in Table XIII. Data show that at a 30 minute residence time, HNCO recovery increased with increase in level of sulfolane distillation. At a 15 minute residence time where greater sulfolane distillation rates were achieved, HNCO recovery was 95%. This suggests that HNCO recovery is a function of the amount of sulfolane readily available for condensation and trapping of volatile HNCO.

TABLE X

VESSEL TEMPERATURE/PRESSURE PROFILE AND TEMPERATURE RECORDING POINT PROFILE FOR CONTINUOUS UREA/BIURET REACTOR/STRIPPER RUNS

| Run No. | Vessel Temp. (°C.)/Press. (mmHg) | | | | | TR1 Point (°C.) | | | | |
|---|---|---|---|---|---|---|---|---|---|---|
| | 11 | 12 | 10 | 20a | 49 | 1[1] | 2 | 3 | 4 | 5[1] |
| 1 | ~25/760 | 120/200 | 195-200/90 | 40-50/90 | ~25/87 | 140-160 | 180-200 | 40-50 | 40-50 | 80-120 |
| 2 | ~25/760 | 120/200 | 196-200/97 | 40-50/97 | ~25/94 | 140-180 | 180-200 | 40-60 | 40-50 | 80-140 |
| 3 | ~25/760 | 120/200 | 194/100 | 40-50/100 | ~25/97 | 140-180 | 190-200 | 40-50 | 40-50 | 60-80 |
| 4 | ~25/760 | 120/200 | 197/98 | 40-50/98 | ~25/95 | 150-170 | 180-190 | 40-50 | 40-50 | 60-90 |
| 5 | ~25/760 | 120/200 | 195/93 | 40-55/93 | ~25/90 | 140-170 | 175-185 | 44-48 | 38-53 | 120 |
| 6 | ~25/760 | 120/200 | 188/94 | 35-42/94 | ~25/90 | 120-140 | 168-185 | 38-42 | 35-43 | 84-94 |
| 7[2] | ~25/760 | 120/200 | 196/96 | 30-46/96 | ~25/94 | 134-148 | 182-192 | 30-36 | 30-46 | 110-130 |
| 8[2,3] | ~25/760 | 120/200 | 196/96 | 32-58/96 | ~25/93 | 136-148 | 184-196 | 32-44 | 38-58 | 110-138 |

[1] Skin Temperature
[2] Heat not applied to line 40
[3] Heat not applied to line 42.

TABLE XI

CONTINUOUS UREA/BIURET REACTOR/STRIPPER DATA

| Run No. | T°C. | Press. (mmHg) | Feed (12) Flow Rate (g/min.) | Heat Input (Watts) | Rxn. Time (Min.) | Stream | Wt (g) | % CA | % Urea | % Biuret | % NH$_3$ | % OCN— |
|---|---|---|---|---|---|---|---|---|---|---|---|---|
| 1 | 195–200 | 90 | 9.4 | 300 | 50 | 12 | 468 | 0.237 | 1.22 | 0.308 | — | — |
|  |  |  |  |  |  | 10 | 183 | 1.52 | 0.160 | 0.059 | 0.021 | — |
|  |  |  |  |  |  | 20 | 285 | 0.104 | 0.820 | — | 0.020 | N.D. |
|  |  |  |  |  |  | 40 | 3404 | N.D. | — | — | 0.100 | — |
| 2 | 196–200 | 97 | 19.5 | 300–500 | 62 | 12 | 1209 | 0.147 | 1.14 | 0.690 | — | — |
|  |  |  |  |  |  | 10 | 586 | 1.14 | 0.120 | 0.024 | 0.0221 | — |
|  |  |  |  |  |  | 20 | 623 | N.D. | — | — | — | 0.006 |
|  |  |  |  |  |  | 40 | 3362 | 0.099 | — | — | — | — |
| 3 | 194 | 100 | 17.7 | 250 | 60 | 12 | 1063 | N.D. | 2.45 | 0.019 | 0.0493 | — |
|  |  |  |  |  |  | 10 | 959 | 0.383 | 0.650 | 0.19 | 0.0187 | N.D. |
|  |  |  |  |  |  | 20 | 146 | 0.101 | 1.27 | 0.840 | 0.0114 | — |
|  |  |  |  |  |  | 40 | 2390 | N.D. | — | — | 0.111 | — |
| 4 | 197 | 98 | 18.0 | 300 | 60 | 12 | 1082 | N.D. | 2.40 | 0.0360 | 0.0191 | — |
|  |  |  |  |  |  | 10 | 878 | 0.50 | 0.490 | 0.110 | 0.0101 | N.D. |
|  |  |  |  |  |  | 20 | 260 | 0.09 | 1.99 | 0.820 | 0.0135 | N.D. |
|  |  |  |  |  |  | 40 | 2298 | N.D. | 0.0464 | — | 0.143 | N.D. |
| 5 | 195 | 93 | 18.3 | 350 | 60 | 12 | 1101 | N.D. | 2.68 | 0.0140 | 0.0053 | N.D. |
|  |  |  |  |  |  | 10 | 688 | 0.74 | 0.453 | 0.276 | 0.0062 | 0.0030 |
|  |  |  |  |  |  | 20 | 474 | 0.13 | 1.70 | 1.88 | 0.0113 | 0.0348 |
|  |  |  |  |  |  | 40 | 2128 | N.D. | 0.0027 | — | — | — |
| 6 | 188 | 94 | 42.3 | 350 | 26 | 12 | 1101 | N.D. | 3.19 | 0.054 | 0.0032 | 0.09 |
|  |  |  |  |  |  | 10 | 951 | 0.580 | 1.22 | 0.738 | 0.0081 | 0.00 |
|  |  |  |  |  |  | 20 | 150 | 0.09 | 1.96 | 1.26 | 0.0154 | 0.007 |
|  |  |  |  |  |  | 40 | 1982 | N.D. | 0.0585 | — | 0.268 | — |
| 7 | 196 | 96 | 36.7 | 475 | 31 | 12 | 1139 | 0.029 | 3.19 | 0.196 | 0.0080 | 0.0015 |
|  |  |  |  |  |  | 10 | 926 | 1.05 | 1.15 | 0.542 | 0.0070 | 0.0006 |
|  |  |  |  |  |  | 20 | 234 | 0.103 | 2.94 | 1.08 | 0.040 | 0.016 |
|  |  |  |  |  |  | 40 | 4487 | N.D. | N.D. | — | 0.161 | — |
| 8 | 196 | 96 | 39.3 | 550 | 29 | 12 | 1139 | 0.017 | 3.41 | 0.140 | 0.0080 | 0.0005 |
|  |  |  |  |  |  | 10 | 730 | 1.08 | 0.750 | 0.670 | 0.0070 | 0.002 |
|  |  |  |  |  |  | 20 | 421 | 0.068 | 2.86 | 1.12 | 0.027 | 0.003 |
|  |  |  |  |  |  | 40 | 4379 | N.D. | N.D. | N.D. | 0.090 | — |

N.D. - None Detected

TABLE XII

EFFECT OF OPERATING CONDITIONS ON UREA/BIURET REMOVAL FROM CONTINUOUS REACTOR/STRIPPER DATA TAKEN OVER TWO RESIDENCE TIMES[3]

| Run No. | Flow Rate (g/min.) | Residence Time (min) | Heat Input (Watts) | % Sulfolane Distilled | Amount Fed (from 12) (g) Urea | Amount Fed (from 12) (g) Biuret | Amount Fed (from 12) (g) HNCO[1] Value | Amount Recovered (from 10) (g) Urea | Amount Recovered (from 10) (g) Biuret | Amount Recovered (from 10) (g) HNCO[1] Value | % Conversion[2] in 10 Urea | % Conversion[2] in 10 Biuret | % Conversion[2] in 10 HNCO[1] Value |
|---|---|---|---|---|---|---|---|---|---|---|---|---|---|
| 1 | 9.4 | 60 | 300 | 60.9 | 5.7 | 1.44 | 5.29 | 0.29 | 0.11 | 0.30 | 96.1 | 92.4 | 94.3 |
| 2 | 19.5 | 29 | 300–500 | 51.5 | 13.8 | 8.34 | 16.9 | 0.70 | 0.14 | 0.62 | 94.9 | 98.3 | 96.3 |
| 3 | 17.7 | 32 | 250 | 13.8 | 26.0 | 0.202 | 18.8 | 6.24 | 1.82 | 5.99 | 76.0 | Gain | 68.1 |
| 4 | 18.0 | 31 | 300 | 24.1 | 26.0 | 0.389 | 19.0 | 4.30 | 0.966 | 3.89 | 83.5 | Gain | 79.5 |
| 5 | 18.3 | 31 | 350 | 43.1 | 29.5 | 0.154 | 21.3 | 3.12 | 1.90 | 3.82 | 89.4 | Gain | 82.0 |
| 6 | 42.3 | 13 | 350 | 13.6 | 35.1 | 0.594 | 25.6 | 11.6 | 7.02 | 14.2 | 67.0 | Gain | 44.7 |
| 7 | 36.7 | 15 | 475 | 20.6 | 36.3 | 2.23 | 27.9 | 10.6 | 5.02 | 11.8 | 70.8 | Gain | 57.7 |
| 8 | 39.3 | 14 | 550 | 37.0 | 38.8 | 1.59 | 29.1 | 5.48 | 4.89 | 8.0 | 85.9 | Gain | 72.5 |

[1](g. Urea × 43.03/60.06) + (g. Biuret × (2×43.03)/103.08)
[2]Grams (IN)-Grams (OUT)/Grams (IN × 100
[3]Reactor/stripper (10) capacity maintained at 500 ml. (558 g.) during each run.

TABLE XIII

RECOVERY OF HNCO VALUES FROM THE CONTINUOUS UREA/BIURET REACTOR/STRIPPER

| Run No. | Sulfolane Distillation Rate (g/min) | HNCO Value[1] Fed (g) | HNCO Value[2] Recovered in 10 g | HNCO Value[2] Recovered in 10 % of Feed | HNCO Value[2] Recovered in 20a g | HNCO Value[2] Recovered in 20a % of Feed | HNCO Value[2] Recovered in 49 g | HNCO Value[2] Recovered in 49 % of Feed | Total HNCO Recovery g | Total HNCO Recovery % of Feed |
|---|---|---|---|---|---|---|---|---|---|---|
| 1 | 5.7 | 5.29 | 1.97 | 37.2 | 1.97 | 37.2 | — | — | >3.94[3] | >74.4[3] |
| 2 | 10.0 | 16.9 | 5.53 | 32.8 | — | — | — | — | — | — |
| 3[4] | 2.4 | 18.8 | 9.66 | 51.4 | 2.50 | 13.3 | — | — | 12.2 | 64.7 |
| 4[4] | 4.3 | 19.0 | 8.28 | 43.7 | 5.49 | 29.0 | 0.77 | 4.1 | 14.5 | 76.8 |
| 5[4] | 7.9 | 21.3 | 8.91 | 41.9 | 14.2 | 66.6 | 0.042 | 0.19 | 23.1 | 108.7 |
| 6[5] | 5.8 | 25.6 | 19.7 | 76.8 | 3.83 | 14.9 | 0.83 | 3.2 | 24.3 | 94.8 |
| 7[5] | 7.5 | 27.9 | 21.2 | 76.0 | 7.32 | 26.2 | N.D.[6] | N.D.[6] | 28.5 | 102.2 |

TABLE XIII-continued

RECOVERY OF HNCO VALUES FROM THE CONTINOUS UREA/BIURET REACTOR/STRIPPER

| Run No. | Sulfolane Distillation Rate (g/min) | HNCO Value[1] Fed (g) | HNCO Value[2] Recovered in 10 g | HNCO Value[2] Recovered in 10 % of Feed | HNCO Value[2] Recovered in 20a g | HNCO Value[2] Recovered in 20a % of Feed | HNCO Value[2] Recovered in 49 g | HNCO Value[2] Recovered in 49 % of Feed | Total HNCO Recovery g | Total HNCO Recovery % of Feed |
|---|---|---|---|---|---|---|---|---|---|---|
| 8[5] | 14.5 | 29.1 | 15.7 | 54.0 | 12.9 | 44.3 | N.D.[6] | N.D.[6] | 28.6 | 98.3 |

[1] as urea + biuret
[2] as urea + biuret + CA + NH₄OCN
[3] without biuret analysis of condenser/scrubber 20a stream
[4] 30 minutes residence time
[5] 15 minutes residence time
[6] Non-Detectable.

I claim:

1. In a process for producing cyanuric acid wherein a compound selected from the group consisting of urea and biuret is heated in an inert solvent to a temperature of at least about 180° C. under a subatmospheric pressure of from about 0 to about 250 mm. of Hg., wherein a reaction mixture (i) comprising cyanuric acid, from about 0.01 to about 5 percent by weight of said compound or of a mixture (ii) of urea and biuret, and inert solvent is obtained, and wherein cyanuric acid substantially free of said compound and of said mixture (ii) of urea and biuret is recovered from said reaction mixture (i), the improvement which comprises
    distilling said reaction mixture (i) at a temperature of from about 150° C. to about 250° C. and at a pressure of from about 70 to about 170 mm of Hg., and collecting a distillate therefrom comprising not more than 60% by volume of said inert solvent together with said compound or a mixture of urea, biuret and cyanuric acid produced therefrom in distillation, and
    recovering from the remaining reaction mixture said cyanuric acid contained therein.

2. The process of claim 1, wherein the inert solvent is an alkyl sulfone of the formula

wherein $R_1$ and $R_2$ are alkyl groups of from 1 to 6 carbon atoms or are each alkylene and with the sulfur atom form a ring of from 2 to 7 atoms.

3. The process of claim 2, wherein the inert solvent is sulfolane.

4. The process of claim 1, wherein said mixture (i) is so distilled at a temperature of from about 180° C. to about 220° C.

5. The process of claim 1, wherein said mixture (i) is so distilled at a pressure of from about 80 to about 120 mm. of Hg.

6. The process of claim 1, wherein said distillate is condensed at a temperature of from about 25° to about 75° C.

7. The process of claim 1, wherein said mixture (i) is so distilled to remove up to about 60 percent by weight of said inert solvent therefrom.

8. The process of claim 1, wherein said mixture (i) is so distilled to remove from about 10 to about 35 percent by weight of said inert solvent therefrom.

9. The process of claim 1, wherein said distillate is removed from said mixture (i) at a rate of from about 1 to about 25 grams per minute.

10. The process of claim 1, wherein said distillate is removed from said mixture (i) at a rate of from about 2 to about 15 grams per minute.

11. In a process for producing cyanuric acid, wherein a compound selected from the group consisting of urea and biuret is heated, in an inert solvent for urea and biuret in which cyanuric acid is only limitedly soluble, to a temperature of at least about 180° C. under a subatmospheric pressure, wherein a reaction mixture (i) comprising cyanuric acid, from about 0.01 to about 5 percent by weight of said compound or of a mixture (ii) of urea and biuret, and inert solvent is obtained, and wherein cyanuric acid is ultimately separated from said reaction mixture, the improvement which comprises:
    distilling said reaction mixture (i) at a temperature of from about 150° C. to about 250° C. and at a pressure of from about 70 to about 170 mm of Hg,
    collecting a distillate from said reaction mixture (i), said distillate comprising not more than 60% by volume of said inert solvent together with said compound or a mixture of urea, biuret and cyanuric acid produced therefrom in distillation while leaving a remaining reaction mixture having the nature of a slurry of purified cyanuric acid in liquid inert solvent, and
    recovering from said remaining reaction mixture said cyanuric acid contained therein.

* * * * *

UNITED STATES PATENT AND TRADEMARK OFFICE
CERTIFICATE OF CORRECTION

PATENT NO. : 4,187,376
DATED : February 5, 1980
INVENTOR(S) : Ronald H. Carlson

It is certified that error appears in the above-identified patent and that said Letters Patent are hereby corrected as shown below:

Column 1, line 50, "$>1\%$ should read --<1%--. Column 2, line 24, "NH$_3$2HNCO" should read --NH$_3$ + 2HNCO--; line 28, "Ca" should read --CA--. Column 3, line 26, "sulfonane" should read --sulfolane--; line 45, "solfolane" should read --sulfolane--. Column 5, table III, under Press (mm.Hg.), "$\Psi$-115" should read --105-115--. Column 7, table VIII, footnote 2 "1.82 Biuret" should read --1.82% Biuret--. Column 12, table XI, Run 4, Stream 20, value under %NH$_3$, "0.0135" should read --0.0136--; table XI, Run 6, Stream 12, value under %OCN- "0.09" should read --0.0004--; table XI, Run 6, Stream 10, value under %OCN- "0.00" should read --0.0004--.

Signed and Sealed this

Fifteenth Day of July 1980

[SEAL]

Attest:

SIDNEY A. DIAMOND

Attesting Officer

Commissioner of Patents and Trademarks